United States Patent [19]

Ito et al.

[11] Patent Number: 5,202,269
[45] Date of Patent: Apr. 13, 1993

[54] METHOD FOR IMMUNOCHEMICAL DETERMINATION OF HAPTEN

[75] Inventors: Michio Ito; Minoru Ogura, both of Yokohama; Hideki Kohno, Kawasaki, all of Japan

[73] Assignee: Mitsubishi Kasei Corporation, Tokyo, Japan

[21] Appl. No.: 592,612

[22] Filed: Oct. 4, 1990

[30] Foreign Application Priority Data

Oct. 6, 1989 [JP] Japan .................. 1-261397

[51] Int. Cl.⁵ .................. G01N 33/553; G01N 33/546
[52] U.S. Cl. .................. 436/526; 436/520; 436/523; 436/525; 436/533; 436/817; 436/822; 435/7.25
[58] Field of Search .............. 436/519, 520, 526, 525, 436/523, 528, 538, 540, 829, 822, 817, 806, 531, 533; 435/7.93, 7.21, 7.25

[56] References Cited

U.S. PATENT DOCUMENTS 4,115,535 9/1978 Giaver .................. 424/1
4,185,084 1/1980 Mochida et al. .............. 435/7.93 X
4,279,617 7/1981 Masson et al. .................. 422/57 X

FOREIGN PATENT DOCUMENTS 0357786 1/1989 European Pat. Off. .............. 33/543
89/04373 5/1989 World Int. Prop. O. .

Primary Examiner—Esther L. Kepplinger
Assistant Examiner—Susan C. Wolski
Attorney, Agent, or Firm—David G. Conlin; Linda M. Buckley

[57] ABSTRACT

A method for immunochemical determination of a hapten in a sample is disclosed, in which (A) a high-molecular compound to which the hapten is bound (reagent A),
(B) insoluble carrier particles carrying thereon an antibody to the hapten (reagent B), and
(C) magnetic substance-containing insoluble carrier particles carrying thereon an antibody to an antigenic determinant in the high-molecular compound and different from the hapten (reagent C), are used. These three reagents are dispersed in the sample, then, a magnetic field is applied to separate from the reaction mixture unreacted reagent (C) and agglutinated particles formed from the reagent (B) and the reagent (C) through the reagent (A). The amount of the reagent (B) remaining dispersed in the reaction mixture is measured, thereby determining the extent of competitive inhibition to the agglutination of the reagent (B) and the reagent (C) through the reagent (A) by the reaction between the hapten in the sample and the reagent (B). The method of the present invention requires no troublesome operations such as separation-washing and is free from any problem is safety. By the method of the present invention, the concentration of a hapten in a sample is determined by simple operations in a short time and with high sensitivity.

20 Claims, 2 Drawing Sheets

METHOD FOR IMMUNOCHEMICAL DETERMINATION OF HAPTEN

BACKGROUND OF THE INVENTION

The present invention relates to a method for determining the amount of a hapten present in a sample by the utilization of antigen-antibody reaction. In particular, it relates to a method for determining a hapten which may be utilized as a clinical analysis such as a serum analysis for determining the blood level of hormones or drugs in a field of medical diagnosis.

A low-molecular compound, which itself is not capable of raising antibody production in a living body, but acts as an antigen and becomes capable of raising antibody production when bound to a high-molecular compound such as protein, is referred to as a hapten. In a field of clinical analysis, immunochemical determination of the concentration of various substances such as low-molecular hormones and drugs in blood is practiced by the utilization of the antibodies obtained in the manner described above using the substances as haptens.

Radioimmunoassay (RIA), enzyme immunoassay (EIA) and fluorescence polarization immunoassay can be cited as principle examples of immunochemical determination techniques for hapten. This classification of the techniques depend on the difference of the labels by which the extent of reaction is determined. From the aspect of operating procedure, the techniques can be classified into so-called B/F separation in which determination is made by separating the reacted (bound) form and the unreacted (free) form of the labeled antigen or labeled antibody, and so-called homogeneous method in which no such separation is required.

The B/F separation method is employed in a part of RIA and EIA. This method is sensitive and specific, but has the defect that it is tedious in operation and requires a long time period for determination, because it involves troublesome separation-washing operations. The increase in frequency of handling a sample during the operations such as separation, washing, etc., leads to a greater risk to infection from the sample. In addition, RIA involves many difficult problems in handling such as the problem of disposal of radioactive wastes and necessity for specific equipments. EIA, because of the use of an enzyme as the label, has the disadvantages that strict control is required for reaction time and temperature, and that the determination tends to be affected by inhibition reactions.

The homogeneous method is employed in fluorescence polarization immunoassay and a part of EIA. This method is simple in operation, relatively short in time required for determination and easy to automate by the utilization of a particular device. However, because of low sensitivity, this method is limited to determination of certain types of drugs and is difficult to determine the substances present in a level of ng/ml such as many types of hormones and digoxin. Further, fluorescence polarization determination requires an expensive apparatus. The homogeneous EIA also has the disadvantages inherent in a method using an enzyme, and it may be said that inhibition reactions are unavoidable in this method because the substances to be determined remains in the system.

Latex agglutination is also a type of homogeneous method. This method is used for determination of a certain type of hapten mainly in a manner of slide method which is a qualitative or semi-quantitative method. In addition to the advantages of homogeneous method, i.e., simple operation and a short determination time, this method has the merit of being excellent in reagent storage stability and stability of reaction system as compared with EIA and other assay methods. However, low detection sensitivity is the greatest defect of this method (Japanese Patent Application Laid-Open (KOKAI) Nos. 53-104726(1978), 55-52945(1980), 55-52946(1980), 55-156866(1980) and 61-265571(1986)).

A method for immunochemical determination of a hapten utilizing latex agglutination as described above, i.e., a method in which the extent of inhibition by hapten against the agglutination of latex particles through a high-molecular compound to which a hapten is bound is determined, has problems in sensitivity. One problem is difficulty to obtain a high titer antibody to a hapten, especially one derived from a living body, while an antibody with a high titer is necessary for effecting the latex agglutination. Another problem is that it is difficult to improve inhibition sensitivity from the methodological reason involved in the method, i.e., the necessity of covering a large portion of an antibody with a hapten for inhibiting the agglutination whereas the antibody present in only a part on the latex particle surface is sufficient for agglutination.

WO 89/01161 discloses a method for determining the concentration of a hapten in a sample, which comprises the steps of:

incubating a mixture of the sample containing the hapten with first magnetically attractable particles carrying the hapten and second particles carrying an antibody to the hapten, applying a magnetic field to the mixture to bring down unreacted first particles and agglutinated particles of the first and second particles, and measuring the optical density of the mixture, thereby determining the concentration of the hapten in the sample from the decrease in turbidity. In this method, also, an antibody with a high titer to the hapten is required, and therefore, a method which is highly sensitive and capable of using an antibody with a lower titer to a hapten has been desired.

SUMMARY OF THE INVENTION

The present inventors together with another inventor have previously invented a measuring method using two types of particles, insoluble carrier particles and magnetic substances-containing insoluble carrier particles, as an application of latex agglutination technique (Japanese Patent Application Laid-Open (KOKAI) No. 1-193647(1989)). The present inventors have continued further studies and reached the idea that it would be possible to improve the inhibition efficiency by carrying an antihapten antibody on only one of the above two types of particles, because it is possible in the method previously invented to change the kind of the antibody to be carried on both the two types of insoluble carrier particles. The present inventors have further reached the idea to carry on the other type of particles an antibody to an antigenic determinant in a high-molecular compound to which the hapten is bound and different from the hapten. This idea has made it possible to use a high-titer antibody as the antibody to a antigenic determinant different from the hapten by appropriately selecting a high-molecular compound of a high antigenecity, thereby making the use of a high-titer antibody to the hapten unnecessary. Thus, the improvement in agglutination activity, which has been a problem in the prior art, has also been realized. The present invention has been accomplished based on these findings.

The specific character of the present invention is in a method for immunochemical determination of the concentration of a hapten in a sample, which comprises the steps of:

dispersing
(A) a high-molecular compound to which the hapten is bound (reagent A),
(B) insoluble carrier particles carrying thereon an antibody to the hapten (reagent B), and
(C) magnetic substance-containing insoluble carrier particles carrying thereon an antibody to an antigenic determinant in the high-molecular compound and different from the hapten (reagent C), in the sample to complete a reaction;

applying a magnetic field to separate from the reaction mixture unreacted reagent (C) and agglutinated particles formed from the reagent (B) and the reagent (C) through the reagent (A); and measuring the amount of the reagent (B) remaining dispersed in the reaction mixture, thereby determining the extent of competitive inhibition to the agglutination of the reagent (B) and the reagent (C) through the reagent (A) by the reaction between the hapten in the sample and the reagent (B).

DETAILED DESCRIPTION OF THE INVENTION

Figure 1:
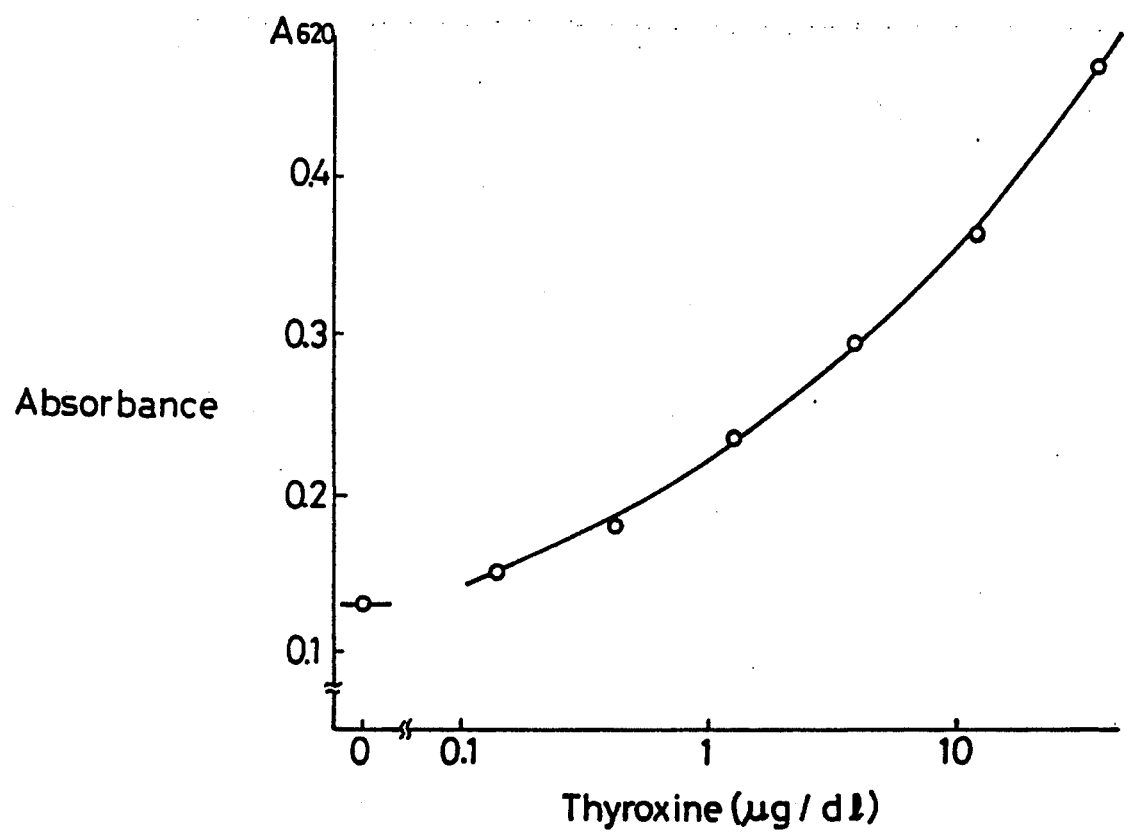
FIG. 1 ia graph showing the relation of the result of measurement of turbidity at 620 nm against thyroxine concentration in the samples.

The term "hapten" used in the present invention refers to a low-molecular substances having a molecular weight of not greater than 10,000 which itself is not capable of raising antibody production in a human or animal body, but becomes capable of raising antibody production when bound to a high-molecular compound such as a protein. This term may also refer to the portion which structurally corresponding to the low-molecular substance when bound to the high-molecular compound. The substance determined as a hapten in clinical examination include a low-molecular hormone such as thyroid hormone including thyroxine, steroid and adrenaline, a small peptide hormone such as gastrin, vasopressin and angiotensin, various kinds of synthetic drugs as digoxin.

the "high-molecular compound" referred to in the present invention mean a compound with a molecular weight of not less than 5,000 which, unlike haptens, has antigenecity being capable of raising antibody production, and which can have a hapten molecule within in its molecular structure or has a functional group capable of binding a hapten molecule chemically. Usually, is used a water-soluble serum protein having a high antigenecity such as bovine serum albumin, equine ferritin and hemocyanin, or a substance, polylysine for example, having a molecular weight from several tens of thousands to several hundreds of thousands, and being highly soluble in water and abundant with functional groups.

As the "insoluble carrier particles", is used a cell such as red blood cell, a microcapsule such as liposome, an organic polymer, an inorganic fine particle such as carbon black or a colloidal particle of various kinds of metals or metal compounds. A synthetic polymer latex particle obtained by the polymerization of an aromatic vinyl compound such as styrene, divinylbenzene, vinyltoluene, etc., and/or a methacrylic ester derivative is more preferred to use. Further, those particles which have an excellent dispersibility in the reaction medium and do not easily settle down are preferred to use for facilitating the optical determination.

The magnetic substance contained in the "magnetic substance-containing insoluble carrier particles" may include iron, a magnetic iron oxide such as triiron tetraoxide and a mixture or alloy of iron or the magnetic iron oxide with other metal or metal oxide. The magnetic substance is preferred to be free from residual magnetism and the average particle size thereof is preferably from 10 to 200 Å. The magnetic substance may be contained in a proportion from 5 to 100% by weight, preferably from 20 to 65% by weight, of the insoluble carrier particle. As the matrix of the insoluble carrier particle containing the magnetic substance, there may be used a polysaccharide such as agarose, dextran and carboxymethylcellulose, a protein such as gelatin and polymerized albumin, and a protein derivative, however, it is more preferred to use a synthetic polymer obtained by the polymerization of an aromatic vinyl compound such as styrene, divinylbenzene, etc. and/or a methacrylic ester derivative.

The average particle size of each of the insoluble carrier particle and the magnetic substance-containing insoluble carrier particle is from 0.1 to 10 μm, preferably 0.2 to 3 μm by considering the determination sensitivity. A combination of the insoluble carrier particles having average particle sizes of 0.5 to 3 μm and the magnetic substance-containing insoluble carrier particles having average particle sizes of 0.2 to 2 μm is preferred.

More preferred is a combination of the insoluble carrier particles having average particle sizes of 1 to 2.5 μm and the magnetic substance-containing insoluble carrier particles having average particle sizes of 0.5 to 1.5 μm. When the average particles sizes of the insoluble carrier particles are too large, the spontaneous sedimentation of the particles would take place in an earlier stage of the determination, and when the average particle sizes of the magnetic substance-containing insoluble carrier particles are too small, the separation by applying a magnetic field would be too time-consuming, both the case being impractical.

Physical adsorption or covalent bonding through a functional group is available for carrying an antibody on both the types of the carrier particles. The amount ratio of the carrier particles to the antibody to be carried is not critically limited, but in many cases good results can be obtained when 5 to 200 times by weight of the carrier particles with respect to the antibody is used for each types of the carrier particles.

Determination of hapten by agglutination inhibition is possible by carrying an antihapten antibody on either the insoluble carrier particles or the magnetic substance-containing insoluble carrier particles. However, a much better result can be obtained when the antihapten antibody is carried on the insoluble carrier particles which are directly related to the optical determination while the antibody to an antigenic determinant in the high-molecular compound different from the hapten is carried on the magnetic substance-containing insoluble carrier particles which contribute more greatly to agglutination activity.

The insoluble carrier particles (reagent B) carrying an antihapten antibody and the magnetic substance-containing insoluble carrier particles (reagent C) carrying an antibody to an antigenic determinant different from the hapten and in the high-molecular compound (reagent A) to which the hapten is bound are mixed with a sample liquid suspected of containing the hapten and a given amount of the reagent A, and allowed to react. A sufficient mixing is necessary at the start of the reaction, however, after uniform mixing is effected, the mixture may be allowed to stand without further mixing to continue the reaction. The reaction can be carried out at a pH of 5 to 10, preferably 7 to 9, as in the ordinary immunochemical reactions. Although the reaction can be carried out at a temperature of 2° to 50° C., preferably carried out at a temperature of room temperature to 37°–40° C. The reaction time can be selected from a wide range of immediately after the start of the reaction to overnight. However, in view of sensitivity and operational advantages, the reaction time is usually 5 to 60 minutes. These reaction conditions are applied in the succeeding steps.

Usually a buffer solution is used for maintaining the desired level of pH. As the buffer solution, may be used a phosphoric acid buffer, tris(hydroxymethyl)aminomethane buffer, etc. However, almost all of the buffer solutions commonly used at a pH from neutral to weakly basic. In many cases, a salt such as sodium chloride and a protein such as bovine serum albumin are added for avoiding non-specific reactions.

When the reagent (B) and the reagent (C) are mixed in a solution containing a given amount of the reagent (A), the reaction between the antihapten antibody on the surface of the reagent (B) and the hapten on the reagent (A), and the reaction between the antigenic determinant on the reagent (A) which is different from the hapten and the antibody to the antigenic determinant carried on the reagent (C) take place, thereby forming agglutinated particles of the reagent (B) and the reagent (C) through the reagent (A).

When a sample suspected of containing the hapten is coexisted in this reaction system, the hapten present in the sample is reacted with the antihapten antibody carried on the reagent (B), resulting in a decrease in the antibody amount on the reagent (B) which reacts with the hapten bound to the reagent (A), thereby inhibiting agglutination of the reagent (B) and the reagent (C) through the reagent (A). Thus, by determining the extent of the inhibition of agglutination, it is possible to know the amount of the hapten in the sample.

In this case, since the extent of competition between the hapten in the sample and the hapten on the reagent (A) against the antihapten antibody on the reagent (B) is determined, it is necessary to take such an order of addition that the reaction between the antihapten antibody on the reagent (B) and the hapten on the reagent (A) do not precede the reaction between the antihapten antibody on the reagent (B) and the hapten in the sample. However, in the formation of agglutination of the reagent (B) and the reagent (C) through the reagent (A), either of the bonding between the reagent (B) and the reagent (A) and the bonding between the reagent (C) and the reagent (A) may precede the other. Therefore, in the actual operation, the antihapten antibody on the reagent (B) may be first reacted with the hapten in the sample and the hapten on the reagent (A), and then the reagent (C) is acted thereon. This order of addition of the reagents may be reversed. Further, it is also possible to mix all of the reagents at the same time and allow to react.

The amount ratio of the insoluble carrier particles and the magnetic substance-containing insoluble carrier particles to be used is preferred, in view of determination sensitivity, in the range of 1:20 to 20:1, more preferably 1:4 to 4:1.

The amount of the reagent (A) used can be appropriately determined based on the kind of the hapten to be determined, the concentration of the hapten in a sample, the titer of the antibody used in the reagents (B) and (C).

The strength of a magnetic field and the configuration and shape of the reaction system are preferably selected so that unreacted reagent (C) and agglutination of the reagents (B) and (C) through the reagent (A) may be separated from the reaction mixture in 5 to 20 minutes. Too short separation time may cause a reduction in sensitivity and reproducibility, while too long separation time deteriorates operability. From these reasons, a reaction system of a relatively small size is easy to operate. For example, a 96-hole microplate is preferred in carrying out the present invention, because individual wells thereof is small in size and it is possible to perform determination with ease by using a microplate reader as in the case of EIA utilizing a microplate when small magnets are placed in the space between the wells.

When the unreacted reagent (C) is separated by application of a magnetic field, there is also separated the reagent (B) which agglutinated with the reagent (C), so that the amount of the reagent (B) which remain unagglutinated as the result of the binding with the hapten can be easily determined by measuring turbidity of the reaction mixture containing the unreacted reagent (B) or the amount of the carrier particles dispersed in the reaction mixture. The greater the amount of the hapten in the sample, the higher the turbidity (absorbance). In some case, a part of the reagent (C) may remain unseparated and may be detected together with the unagglutinated reagent (B), but this is no problem if the extent thereof is of no practical significance.

It would be the simplest way of optical detection to observe with the naked eye the difference in turbidity depending upon the remaining amount of the reagent (B) on a black background under a lighting. Quantitative assays are possible by using various types of colorimeter or turbidimeter. As to the wavelength of measuring light, a wavelength in the range corresponding to visible light or near infrared ray, preferably 600 to 1100 nm, is used. The number of the remaining particles may be directly counted by flow cytometry using laser light.

A calibration curve of the hapten can be obtained by measuring a quantitatively detectable parameter such as turbidity of samples of various known hapten concentrations, then, plotting the quantitative value of the parameter against the hapten concentration. By reference to the calibration curve obtained, the amount of the hapten in a sample of unknown concentration can be quantitatively determined.

The present invention will be described more particularly below referring to the Examples. It is to be understood, however, that these Examples are merely intended to be illustrative and not to be construed as limiting the scope of the present invention.

EXAMPLE 1

Determination of Thyroxine

Thyroglobulin is a natural thyroxine binding high-molecular substance having several molecules of thyroxine residue in one molecule. For the purpose of enhancing specificity of the reaction between the antigenic determinant different from hapten on the high-molecular compound and the antibody to the antigenic determinant, theophylline with strong antigenicity was bound to thyroglobulin and used as antigenic determinant on the high-molecular compound.

Preparation of Reagents

1) Preparation of latex carrying antithyroxine antibody F(ab')$_2$

Rabbits were immunized against thyroxine binding bovine serum albumin prepared according to the method of H. Gharib et. al. (J. Clin. Endocrinol. Metab., 33, 509, (1971)). The obtained antiserum was absorbed on bovine serum albumin, and anti-IgG antibody fraction was collected from the obtained thyroxine specific antiserum, digested with pepsin and subjected to a molecular sieve column chromatography to obtain F(ab')$_2$. In 10 ml of 0.1M tris buffer (pH 8) (hereinafter referred to as "tris buffer"), was dissolved 4 mg of F(ab')$_2$. The resulting antibody solution was mixed under stirring for 30 minutes with a 2% suspension of polyvinyltoluene latex (produced by SERADYN, INC.) having a particle size of 2.02 $\mu$m, which had been prepared using the tris buffer solution, thereby carrying the antithyroxine antibody F(ab')$_2$ on the latex surface. The mixture was centrifuged at 10,000 r.p.m. for 10 minutes to remove the supernatant. Thereafter, the mixture was added with 20 ml of the tris buffer containing 0.3% of bovine serum albumin and re-dispersed by 30-minute stirring followed by an ultrasonic treatment to ensure a fine dispersion for stabilizing the latex. After further centrifugated, the resultant latex was dispersed and suspended in 20 ml of the tris buffer containing 0.05% of sodium azide and preserved at 4° to 10° C.

2) Preparation of magnetic substance-containing latex carrying a mouse antitheophylline monoclonal antibody A mixture of 1 ml of a magnetic substance-containing latex (Estapor SML266, particle size: 0.7 $\mu$m, 10%, produced by Rhone poulenc chimie) with 19 ml of distilled water, after well mixed, was centrifuged at 10,000 r.p.m. for 10 minutes and then the supernatant was removed to obtain washed latex pellets. To the pellets was added an antibody solution dissolved 4 mg of an antitheophylline monoclonal antibody (produced by Cambridge Medical Diagnostic Co., Ltd.) in 10 ml of the tris buffer to redisperse, followed by one-hour stirring to carry the antibody on the surface of the magnetic substance-containing latex. The dispersion was centrifugated again to remove the supernatant followed by redispersing and suspending in 10 ml of the tris buffer containing 0.3% of bovine serum albumin for stabilization. The resultant dispersion was further centrifuged, suspended in 10 ml of the tris buffer containing 0.05% of sodium azide and preserved at 4° to 10° C.

3) Preparation of theophylline binding bovine thyroglobulin

A theophylline derivative was synthesized according to the method of C. E. Cook et. al. (Res. Comm. Chem. Path. Pharm., 13, 497 (1976)). 5 mg of the theophylline derivative was reacted with 100 mg of bovine thyroglobulin, and the unreacted theophylline derivative was removed by a molecular sieve gel chromatography to obtain theophylline binding bovine thyroglobulin.

Procedure of Determination

A thyroxine solution (33.3 $\mu$g/dl) was diluted sequentially by 3-fold with a 0.1M tris-hydrochloric acid buffer containing 0.1% of bovine serum albumin and 0.9% of common salt (pH 8.2, hereinafter referred to as "TBS buffer") to prepare a diluted series of samples with the lowest concentration of 0.137 $\mu$g/dl. Each of the samples of the diluted series was apportioned into two wells of a 96-hole microplate in an amount of 50 $\mu$l. The same was repeated with TBS buffer as control. Then 100 $\mu$l of TBS buffer containing 10 ng/ml of theophylline binding thyroglobulin and 0.06% of ammonium 8-anilino-1-naphthalenesulfonate was apportioned into each of the wells in which the samples had already been apportioned. Then 25 $\mu$l of a suspension prepared by diluting the latex carrying antithyroxine antibody F(ab')$_2$ four times with the tris buffer was apportioned into each well, and immediately thereafter, a side of the microplate was tapped for about 10 seconds to mix the contents in the wells. The mixture was allowed to stand at room temperature for 60 minutes to complete the reaction. Then 25 $\mu$l of a suspension prepared by diluting the magnetic substance-containing latex carrying an antitheophylline antibody to 5 times with the tris buffer was apportioned into each well, and a side of the microplate was tapped for mixing the contents in the wells. The mixture was then allowed to stand at room temperature for 20 minutes, to complete the reaction. Then, by means of small sized rod magnets of 3 mm$\phi$ a magnetic field was applied to four sides of each wells of the microplate for 10 minutes to draw the magnetic substance-containing latex to the side wall of each well. The turbidity of the mixture in each well, containing the latex carrying antithyroxine antibody F(ab')$_2$ which remained unagglutinated with the magnetic substance-containing latex in each well, was determined by using a microplate reader (NJ-2000, mfd. by Nippon Intermed Co., Ltd.) at a wavelength of 620 nm.

The results are shown in FIG. 1 in terms of relation between thyroxine concentration of each sample and turbidity (calibration curve). The results show that the method of the present invention has a significantly high sensitivity of determination of thyroxine at a level much lower than 6 $\mu$g/dl which is the lower limit of normal range of blood thyroxine.

EXAMPLE 2

Determination of Digoxin

Digoxin is a strong cardiac, but because of low effective concentration in blood and small difference in therapeutic concentration and toxic concentration, it is reckoned as typical example of the drugs which require an accurate determination with high sensitivity.

Preparation of Reagents

1) Preparation of latex carrying mouse antidigoxin monoclonal antibody

In 10 ml of 0.1M tris buffer (pH 8) (hereinafter referred to as "tris buffer"), was dissolved 4 mg of a mouse antidigoxin monoclonal antibody (produced by Cambridge Medical Diagnostic Co., Ltd.). The resulting antibody solution was mixed under stirring for 30 minutes with a 2% suspension of polyvinyltoluene latex (produced by SERADYN, INC.) having a particle size of 2.02 μm, which had been prepared using the tris buffer solution, thereby carrying the mouse antidigoxin monoclonal antibody on the latex surface. The mixture was centrifuged at 10,000 r.p.m. for 10 minutes to remove the supernatant. Thereafter, the mixture was added with 20 ml of the tris buffer containing 0.3% of bovine serum albumin and re-dispersed by 30-minute stirring followed by an ultrasonic treatment to ensure a fine dispersion for stabilizing the latex. After further centrifugated, the resultant latex was dispersed and suspended in 20 ml of the tris buffer containing 0.05% of sodium azide and preserved at 4° to 10° C.

2) Preparation of magnetic substance-containing latex carrying anti-equine ferritin antibody F(ab')$_2$ Anti-IgG antibody fraction was collected from the rabbit anti-equine ferritin antibody (produced by DAKO JAPAN CO., LTD.), digested with pepsin and subjected to a molecular sieve column chromatography to obtain F(ab')$_2$. A mixture of 1 ml of a magnetic substance-containing latex (Estapor SML266, particle size: 0.7 μm, 10%, produced by Rhone poulenc chimie) with 19 ml of distilled water, after well mixed, was centrifuged at 10,000 r.p.m. for 10 minutes and then the supernatant was removed to obtain washed latex pellets. To the pellets was added an antibody solution dissolved 4 mg of the anti-equine ferritin antibody F(ab')2 prepared above in 10 ml of the tris buffer to re-disperse, followed by one-hour stirring to carry the antibody on the surface of the magnetic substance-containing latex. The dispersion was centrifugated again to remove the supernatant followed by redispersing and suspending in 10 ml of the tris buffer containing 0.3% of bovine serum albumin for stabilization. The resultant dispersion was further centrifuged, suspended in 10 ml of the tris buffer containing 0.05% of sodium azide and preserved at 4° to 10° C.

3) Preparation of digoxin binding equine ferritin

Digoxin was subjected to periodide oxidation according to the method of T. W. Smith et. al. (Biochemistry, 9, 331, (1970)) to convert the saccharide chain end into aldehyde, then reacted with equine ferritin followed by reduction. The unreacted substances were removed by dialysis to obtain digoxin binding equine ferritin.

Procedure of Determination

A digoxin solution (328 ng/ml) was diluted sequentially by 3-fold with a 0.1M tris-hydrochloric acid buffer containing 0.1% of bovine serum albumin and 0.9% of common salt (pH 8.2, hereinafter referred to as "TBS buffer") to prepare a diluted series of samples with the lowest concentration of 1.35 ng/ml. Each of the samples of the diluted series was apportioned into two wells of a 96-hole microplate in an amount of 100 μl. The same was repeated with TBS buffer as control. Then 100 μl of TBS buffer containing 10 ng/ml of digoxin binding equine ferritin was apportioned into each of the wells in which the samples had already been apportioned. Then 25 μl of a suspension prepared by diluting the latex carrying antidigoxin antibody to four times with the tris buffer was apportioned into each well, and immediately thereafter, a side of the microplate was tapped for about 10 seconds to mix the contents in the wells. The mixture was allowed to stand at room temperature for 60 minutes to complete the reaction. Then 25 μl of a suspension prepared by diluting the magnetic substance-containing latex carrying an anti-equine ferritin antibody to 5 times with the tris buffer was apportioned into each well, and a side of the microplate was tapped for mixing the contents in the wells. The mixture was then allowed to stand at room temperature for 20 minutes to complete the reaction. Then, by means of small sized rod magnets of 3 mmφ a magnetic field was applied to four sides of each wells of the microplate for 10 minutes to draw the magnetic substance-containing latex to the side wall of each well. The turbidity of the mixture in each well, containing the latex carrying antidigoxin antibody which remained unagglutinated with the magnetic substance-containing latex in each well, was determined by using a microplate reader (NJ-2000, mfd. by Nippon Intermed Co., Ltd.) at a wavelength of 620 nm.

Figure 2:
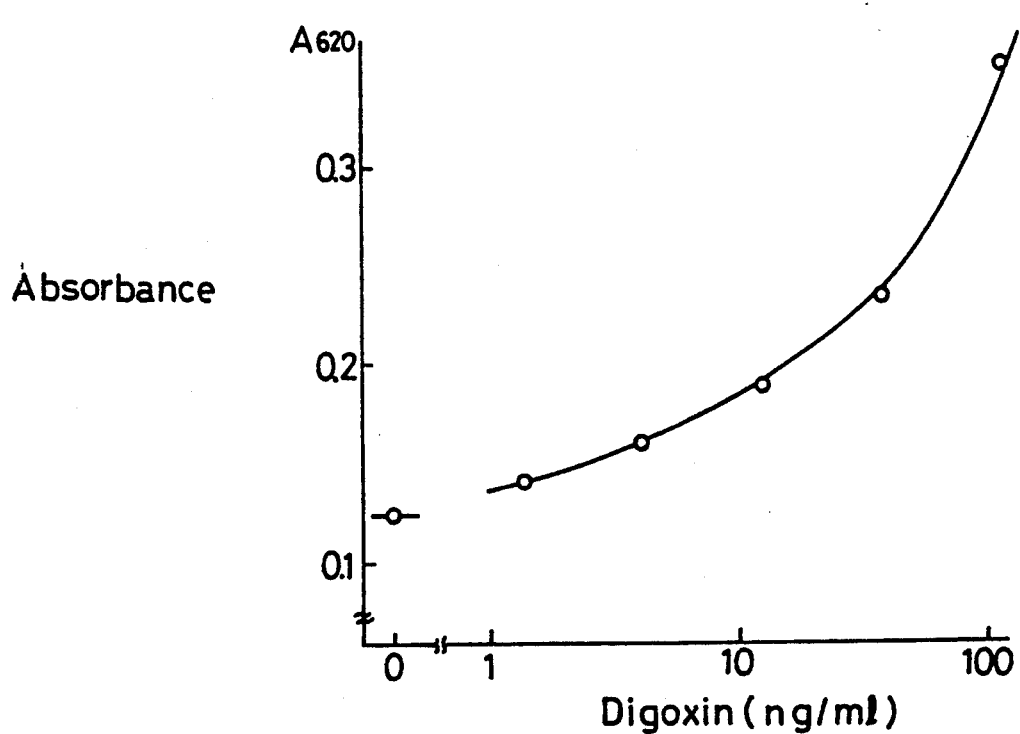
FIG. 2 is a graph showing the relation of the result of measurement of turbidity at 620 nm against digoxin concentration in the samples.

The results are shown in FIG. 2. The results show that the method of the present invention is sufficiently applicable to the digoxin concentration range including 2.2 ng/ml which is the upper limit of therapeutical range of digoxin concentration.

What is claimed is:

1. A method for immunochemical determination of the concentration of a hapten in a sample, comprising the steps of:
    dispersing
    (A) a high-molecular weight compound to which the hapten is bound (reagent A),
    (B) insoluble carrier particles carrying thereon an antibody which specifically binds the hapten (reagent B), and
    (C) magnetic substance-containing insoluble carrier particles carrying thereon an antibody which specifically binds an antigenic determinant in the high-molecular compound and different from the hapten (reagent C),
    in the sample to form a reaction mixture;
    applying a magnetic field to separate from the reaction mixture unreacted reagent (C) and agglutinated particles formed from the reagent (B) and the reagent (C) through the reagent (A); and
    correlating the amount of the reagent (B) remaining dispersed in the reaction mixture, with the concentration of hapten in the sample.

2. The method according to claim 1, wherein the hapten is a low-molecular weight hormone, a small peptide hormone or a synthetic drug.

3. The method according to claim 2, wherein the low-molecular weight hormone is a thyroid hormone, a steroid or adrenaline.

4. The method according to claim 2, wherein the small peptide hormone is gastrin, vasopressin or angiotensin.

5. The method according to claim 1, wherein the high-molecular weight compound has a molecular weight of not lower than 5,000, is antigenic and is capable of binding the hapten or has a functional group capable of chemically binding the hapten.

6. The method according to claim 5, wherein the high-molecular weight compound is bovine serum albumin, equine ferritin, hemocyanin or polylysine.

7. The method according to claim 1, wherein the insoluble carrier particle is non-magnetic and is a cell, a microcapsule, an organic polymer, an inorganic fine particle, or a colloidal particle of a metal or a metal compound.

8. The method according to claim 7, wherein the organic polymer is one obtained by the polymerization of an aromatic vinyl compound, a methacrylic ester derivative, or a combination of an aromatic vinyl compound and a methacrylic ester derivative.

9. The method according to claim 1, wherein the magnetic substance-containing insoluble carrier particle contains a magnetic substance in an amount at least 5% by weight.

10. The method according to claim 9, wherein the magnetic substance-containing insoluble carrier particle contains the magnetic substance in an amount from 20 to 65% by weight.

11. The method according to claim 1, wherein the average particle size of the magnetic substance contained in the magnetic substance-containing insoluble carrier particle is from 10 to 200 Å.

12. The method according to claim 1, wherein the magnetic substance-containing insoluble carrier particle comprises a matrix which is a polysaccharide, a protein, a protein derivative or synthetic polymer.

13. The method according to claim 12, wherein the synthetic polymer is one obtained by the polymerization of an aromatic vinyl compound, a methacrylic ester derivative, or a combination of an aromatic vinyl compound and a methacrylic ester derivative.

14. The method according to claim 1, wherein the average particle size of either the insoluble carrier particle or the magnetic substance-containing insoluble carrier particle is from 0.1 to 10 μm.

15. The method according to claim 14, wherein the average particle size is from 0.2 to 3 μm.

16. The method according to claim 1, wherein the average particle size of the insoluble carrier particle is from 0.5 to 3 μm and the average particle size of the magnetic substance-containing carrier particle is from 0.2 to 2 μm.

17. The method according to claim 16, wherein the average particle size of the insoluble carrier particle is from 1 to 2.5 μm and the average particle size of the magnetic substance-containing carrier particle is from 0.5 to 1.5 μm.

18. The method according to claim 1, wherein the ratio of the amounts of the insoluble carrier particle and the magnetic substance-containing insoluble carrier particle to be added to the sample is 1:20 to 20:1.

19. The method according to claim 18, wherein the ratio is 1:4 to 4:1.

20. The method according to claim 1, wherein the average particle size of the insoluble carrier particle is 1 to 2.5 μm, the average particle size of the magnetic substance-containing insoluble carrier particle is 0.5 to 1.5 μm, and the ratio of the amounts of the insoluble carrier particle and the magnetic substance-containing insoluble carrier particle to be added to the sample is 1:(0.8 to 2).

* * * * *